United States Patent [19]
Walters

[11] Patent Number: 5,651,777
[45] Date of Patent: Jul. 29, 1997

[54] OSTOMY POUCH SUPPORT

[76] Inventor: Wanda K. Walters, P.O. Box 292376, Phelan, Calif. 92329

[21] Appl. No.: 697,489

[22] Filed: Aug. 26, 1996

[51] Int. Cl.$^6$ .................................................. A61F 5/44
[52] U.S. Cl. ................................................ 604/345
[58] Field of Search ................................ 604/332, 345, 604/179; 2/312; 248/95

[56] References Cited

U.S. PATENT DOCUMENTS

| | | |
|---|---|---|
| 4,495,662 | 1/1985 | Miller . |
| 4,533,355 | 8/1985 | Fair . |
| 4,888,006 | 12/1989 | Beaupied . |
| 5,026,362 | 6/1991 | Willett . |
| 5,135,519 | 8/1992 | Helmer . |

*Primary Examiner*—Robert A. Clarke

[57] ABSTRACT

A supporting device for the ostomy pouch having a waist belt with a length adjuster, an attaching means for connecting ends, an attaching means for attaching the belt to the sling. The sling can have attaching means compatible to that on the belt. An attaching means to close the sling and a C-shaped cut to allow better coverage of the pouch over the stoma area. The invention is designed to hold and support the ostomy pouch in a horizontal fashion across the abdomen.

14 Claims, 2 Drawing Sheets

OSTOMY POUCH SUPPORT

BACKGROUND

The present invention relates to ostomies and means for supporting same.

Currently, there are no ostomy pouch supports, other than underwear on the market. Consequently, ostomy pouches are typically worn hanging down vertically toward the leg, being suspended from the stoma. There are a number of problems with ostomy pouches as conventionally worn. For example:

1. As the pouch fills, the weight tugs on the stoma, an unnatural bulge is created on one side, the pouch has a "slapping" effect against the leg as the user walks, and the pouch moves to uncomfortable places on the body when sitting or sleeping;
2. Because of the above affects, the user will empty the pouch more often in an effort to ease these discomforts, causing yet further inconvenience;
3. It presents a need to wear a different style and type of clothing in an effort to conceal this unnatural looking bulge.

While not being marketed, there are disclosures of ostomy supports in the prior art. See, for example, U.S. Pat. No. 5,135,519 to Helmer, which discloses a belted shielding member and a waste receiver receptacle. U.S. Pat. No. 5,026,362 to Willett discloses an ostomy bag holder having a pouch, the pouch including front and back panels. The back panel has a cut-out for accessing the stoma, lower portions of the panels forming a pocket, upper portions of the panels being releasably connected by fasteners.

In the prior art, supports have been in some cases cumbersome, expensive or restrictive, and in all prior art have failed to achieve a truly comfortable and natural look. All prior art has attempted to support the pouch of ostomies in a vertical position, thereby failing to elevate an unnatural looking vertical bulge and a bulge hanging vertical will hinder comfort in sitting, walking and wearing of some normal clothing. Prior art supports are also comprised of a "one piece" supporting device, thereby causing it to be costly if the user would like to have daily changes of the support covering the ostomy pouch. Since the prior art has not been successful in achieving total comfort with support, there are presently no supports on the market leaving the above problems to be dealt with ostomates.

Thus there is a need for an ostomy pouch support that overcomes the disadvantages of the prior art.

SUMMARY

The present invention meets this need by supporting an ostomy pouch horizontally across the abdomen, without straining the stoma. In one aspect of the invention, an ostomy pouch support for an ostomy patient having an abdominal stoma includes a belt having means for securing about the patient's abdomen above the stoma; a sling member having front and rear walls and a side opening for receiving an ostomy pouch; and means for connecting upper extremities of the front and rear walls of the sling member to the belt, whereby the ostomy pouch is supportable proximate the abdomen.

The rear wall of the sling member preferably has a generally C-shaped clearance cutout extending laterally from the side opening for clearing the stoma. The sling member can be formed of flexible sheet material that extends between the front and rear walls along respective bottom extremities thereof. The means for connecting can include a horizontally disposed seam connecting the front and rear walls proximate upper extremities thereof. The means for connecting can include a mating pair of fastener members, respective ones of the fastener members being secured to the belt and to the sling member. The fastener members can be respective pluralities of male and female snaps.

The belt preferably includes an elastic member for maintaining tension during expansion and contraction of the patient's abdomen. The belt can include an adjustable loop portion at one end thereof, and a belt connector slidably engaging the loop portion, the belt connector releasably engaging an opposite end portion of the belt. The opposite end portion of the belt can have a fixed loop formed therein, the belt connector having a hook extremity for engaging the fixed loop. The side opening can be a main side opening, the sling member having a secondary side opening opposite the main side opening for permitting a portion of the ostomy pouch to extend from the sling member opposite the main side opening.

In another aspect of the invention, a method for supporting an ostomy pouch of a ostomy patient having an abdominal stoma, includes the steps of:

(a) providing an abdominal belt;
(b) securing the belt about the patient above the stoma;
(c) providing a sling member having front and rear walls and a side opening;
(d) supporting the sling member in depending relation to the belt; and
(e) inserting the ostomy pouch into the sling member in parallel-spaced relation to the belt.

The method can include the further steps of:

(a) providing a C-shaped clearance cutout in the rear wall of the sling member and extending from the side opening; and
(b) locating the sling member with the stoma extending within the clearance cutout.

The step of supporting the sling member can include releasably connecting the sling member along an upper marginal edge thereof to the belt.

This support holds the ostomy pouch horizontally across the abdomen so that as the pouch fills, it does so more evenly, thus allowing the user to benefit more from pouch capacity, reducing the amount of times per day the user must empty. With this support, the pouch is equally supported horizontally, thus bulging is minimized and what bulging does occur from a full pouch is a natural look and feel. With this support, there is no tugging on the stoma, and normal clothing styles work well. This support brings about a more normal look and feel and improves every aspect of having an ostomy.

DRAWING

These and other features, aspects, and advantages of the present invention will become better understood with reference to the following description, appended claims, and accompanying drawings, where:

DESCRIPTION

Figures 1A, 1B:
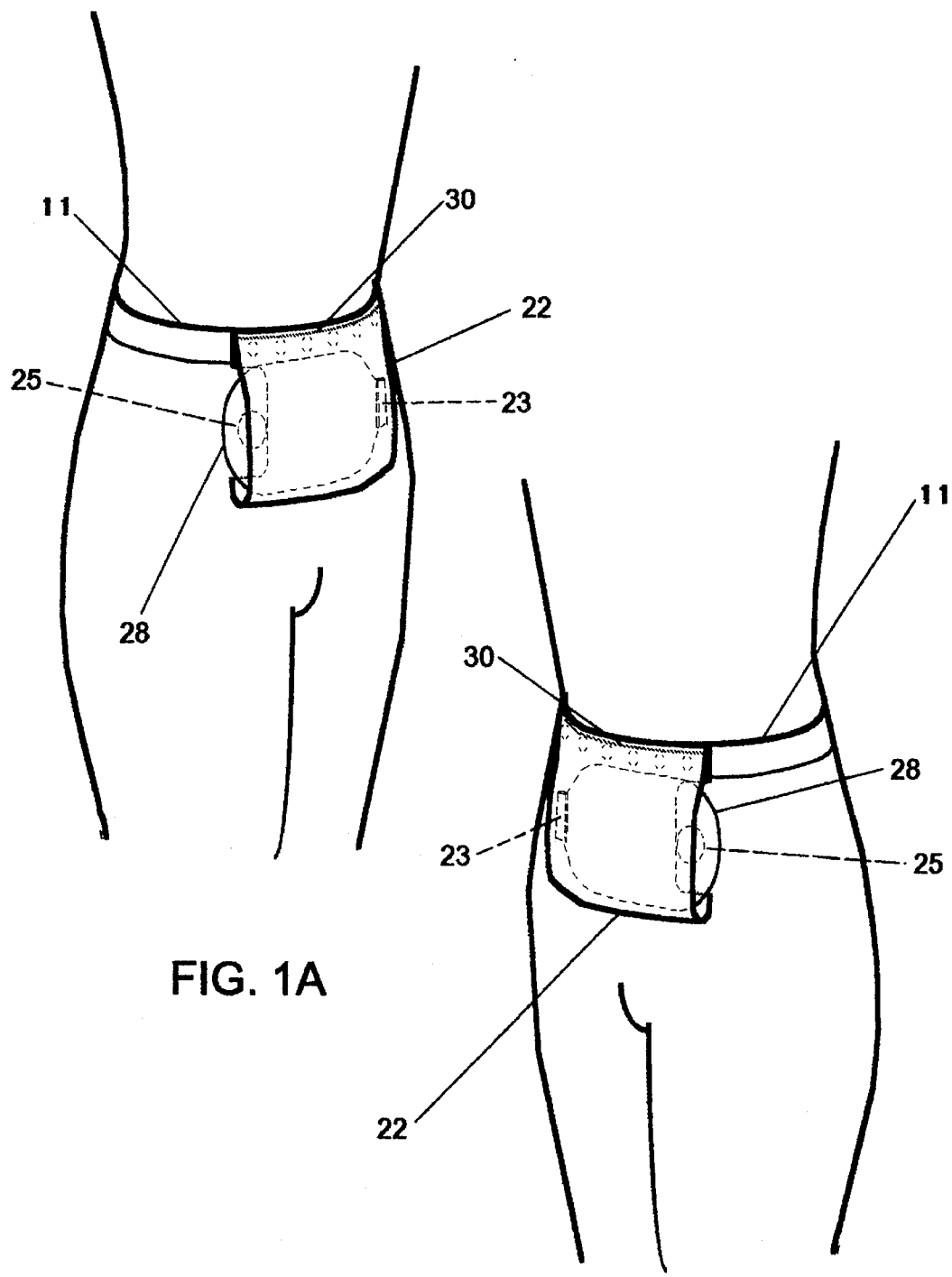
FIG. 1A is a perspective view showing belt and sling parts of an ostomy pouch support according to the present invention in operative relation to a user thereof.
FIG. 1B is a perspective view showing the pouch support of FIG. 1A in a laterally reversed orientation.
Figure 2:
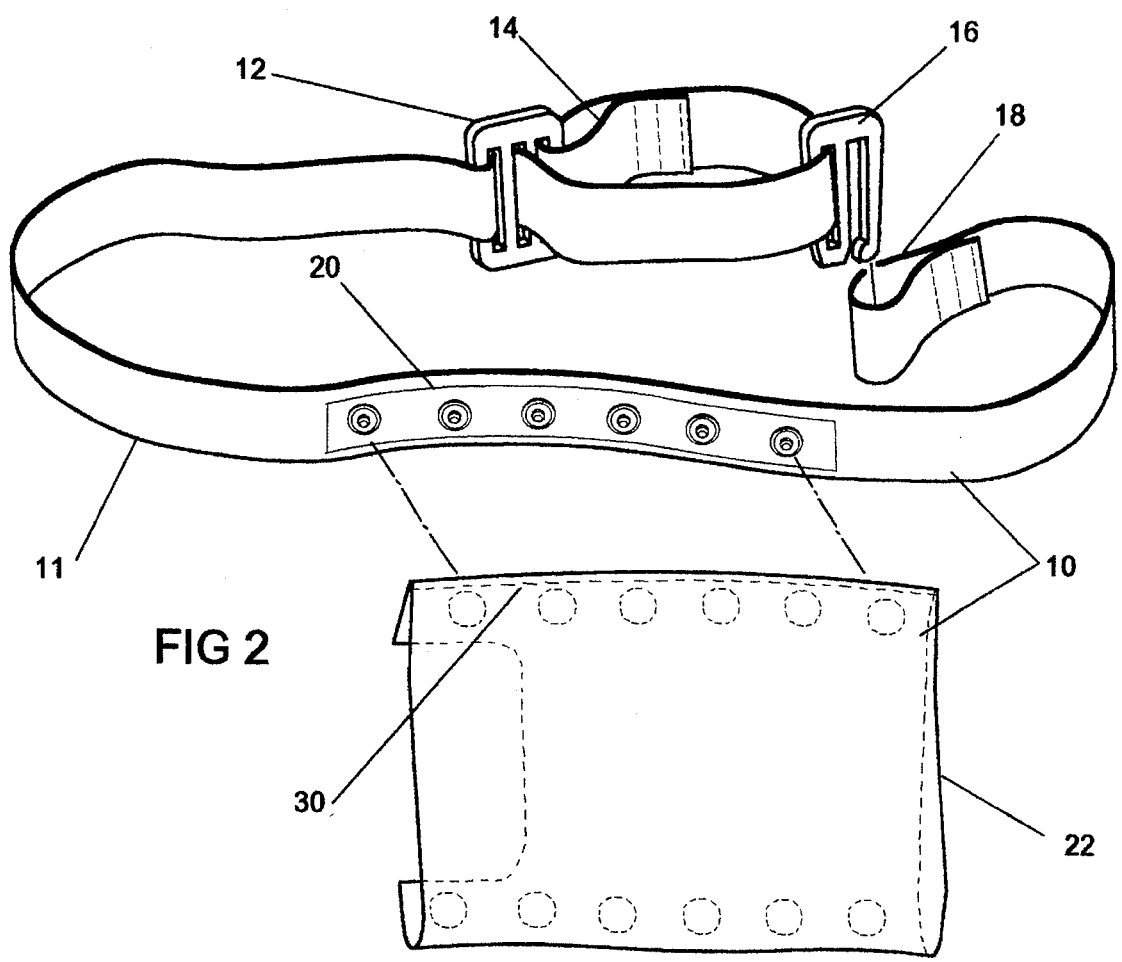
FIG. 2 is a front oblique exploded elevational view of the ostomy pouch support of FIG. 1.

The present invention is directed to an ostomy pouch support that relieves strain on the stoma, and is comfortable to wear and easy to use. With reference to FIGS. 1–4 of the drawings, an ostomy pouch support 10 according to the present invention includes a waist belt 11 that is preferably made of ¾" or 1" elastic. While the belt 11 is contemplated to be made in various sizes (small, medium, large, etc.), it has a length adjuster 12 attached so each size can be made smaller or larger as needed. One end of the belt 11 is woven into one "bay" of the adjuster 12 and brought out again and sewn to itself, creating a loop 14. A bra hook 16 (commonly used in bathing suits) is placed on the belt 11. The open end of the belt 11 is now woven into a second "bay" of the adjuster 12 and out of a third "bay", the end of the belt 11 being sewn to itself, thereby creating a loop 18 for fastening to the bra hook 16.

Figures 3, 4:
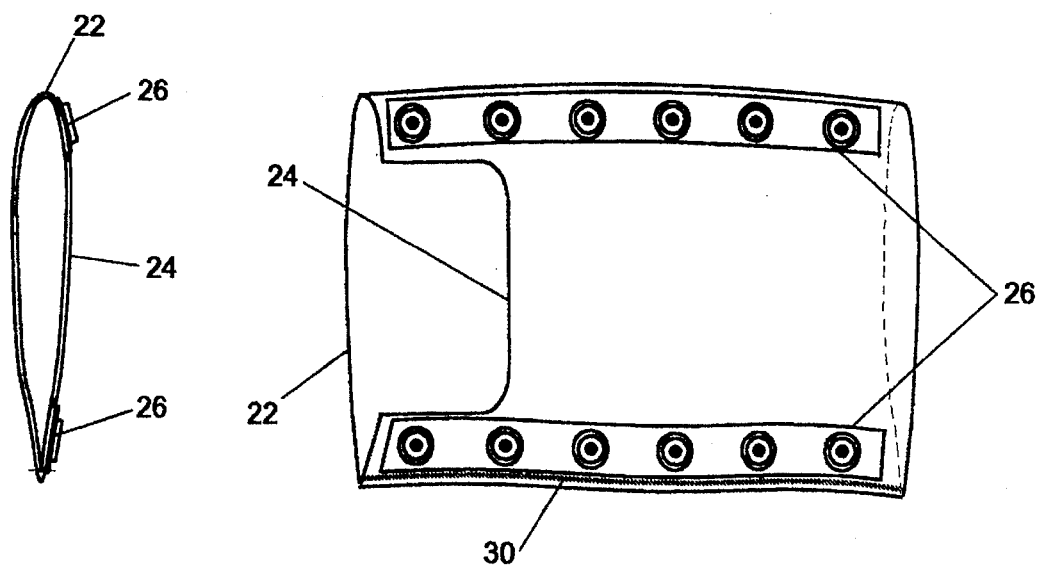
FIG. 3 is an inverted oblique elevational view of the sling portion of the ostomy pouch support of FIG. 1.
FIG. 4 is an end view of the sling portion of FIG. 3.

In the mid-front section of the belt 11 is sewn a male snap tape 20. The purpose for using a snap tape rather than individual snaps is to keep snaps equally spaced, even when elastic is stretched. The ostomy pouch support also includes a sling 22 that can be made of any soft washable material such as a cotton or blend knit. The sling 22 is also contemplated to be made in various sizes. One size is a 6 inch sling as shown in FIG. 1. The finished length of a 6 inch sling is 12 inches (opened) and 8 inches wide top and bottom. There is a clearance or C-shaped cut 24 placed 2 inches down from the top left side of the sling 22, cutting toward the center 1.5 inches down vertically 4 inches, and back to the left side again a clearance opening for a wearer's stoma 25. The preceding measurements are finished measurements. An extra ¼" must be added to all outside dimensions to allow for seams. To the outside top of the sling 22 is sewn a 1.5 female snap tape 26 to the belt 11. The two ends of the sling 22 are then brought together by an attaching means such as a connecting seam 30. Preferably a counterpart of the female snap tape 26 is sewn proximate the bottom of the sling as best shown in FIG. 3. The purpose of the second female snap tape 26 is to provide a reversible connection to the belt 11 whereby the "C" shaped cut can be located on either side of the user.

In preparation for using the ostomy pouch support, a conventional seal ring (not shown) is placed over the stoma 25 in a fashion that allows the pouch 28 to be placed horizontally across the abdomen. The waist belt 11 is placed around the waist and fastened together by placing the bra hook 16 into the hook loop 18. The sling 22 is attached to the waist belt 11 by snapping the female snap tape 20 and the male snap tape 26 together. Place the ostomy pouch 28 into the center of the sling 22, snuggling the C-shaped cut 24 up against the stoma 25.

A pouch clamp 23 may be turned upward into a horizontal position for added comfort if desired. To expose the pouch 28 for emptying, simply slide the support 10 away from the stoma 25 and pouch 28, empty and replace the support by sliding it back into position and reinserting the pouch 28.

Important advantages of the present invention are no "one-sided" unnatural looking bulge, no "slapping" of the pouch 28 against the leg, no need to buy special clothing, no plastic pouch against the skin, no weight tugging against the stoma 25, more pouch capacity benefit, less frequent emptying, more natural look and feel, and more comfort overall.

Although the present invention has been described in considerable detail with reference to certain preferred versions thereof, other versions are possible. For example, the waist belt 11 can be made of stretch or non-stretchable material and can be made with or without the length adjuster 12, and may have many types of closures. The waist belt 11 may also be made in many different widths, etc. The sling 22 may be made from many different types of material, may be made with or without the C-shaped cut 24. The sling 22 can be made to hold the pouch 28 straight horizontally or tilted. The sling 22 may be closed by many types of attaching means as well as means of attaching the sling 22 to the waist belt 11, etc. Therefore, the spirit and scope of the appended claims should not necessarily be limited to the description of the preferred versions contained herein.

What is claimed is:

1. An ostomy pouch support for an ostomy patient having an abdominal stoma, comprising:
   (a) a belt having means for securing about the patient's abdomen above the stoma;
   (b) a sling member having front and rear walls and a side opening for receiving an ostomy pouch; and
   (c) means for connecting upper extremities of the front and rear walls of the sling member to the belt, whereby the ostomy pouch is supportable proximate the abdomen.

2. The ostomy pouch support of claim 1, wherein the rear wall of the sling member has a generally C-shaped clearance cutout extending laterally from the side opening for clearing the stoma.

3. The ostomy pouch support of claim 1, wherein the sling member is formed of flexible sheet material, the material extending between the front and rear walls along respective bottom extremities thereof.

4. The ostomy pouch support of claim 3, wherein the means for connecting comprises a horizontally disposed seam connecting the front and rear walls proximate upper extremities thereof.

5. The ostomy pouch support of claim 1, wherein the means for connecting comprises a mating pair of fastener members, respective ones of the fastener members being secured to the belt and to the sling member.

6. The ostomy pouch support of claim 5, wherein the fastener members are respective pluralities of male and female snaps.

7. The ostomy pouch support of claim 1, wherein the belt comprises an elastic member for maintaining tension during expansion and contraction of the patient's abdomen.

8. The ostomy pouch support of claim 7, wherein the belt includes an adjustable loop portion at one end thereof, and a belt connector slidably engaging the loop portion, the belt connector releasably engaging an opposite end portion of the belt.

9. The ostomy pouch support of claim 8, wherein the opposite end portion of the belt has a fixed loop formed therein, the belt connector having a hook extremity for engaging the fixed loop.

10. The ostomy pouch support of claim 1, wherein the side opening is a main side opening, the sling member having a secondary side opening opposite the main side opening for permitting a portion of the ostomy pouch to extend from the sling member opposite the main side opening.

11. A method for supporting an ostomy pouch of an ostomy patient having an abdominal stoma, comprising the steps of:
   (a) providing an abdominal belt;

(b) securing the belt about the patient above the stoma;

(c) providing a sling member having front and rear walls and a side opening;

(d) supporting the sling member in depending relation to the belt; and (e) inserting the ostomy pouch into the sling member in parallel-spaced relation to the belt.

12. The method of claim 11, comprising the further steps of:

(a) providing a C-shaped clearance cutout in the rear wall of the sling member and extending from the side opening; and (b) locating the sling member with the stoma extending within the clearance cutout.

13. The method of claim 11, wherein the step of supporting the sling member comprises releasably connecting the sling member along an upper marginal edge thereof to the belt.

14. An ostomy pouch support for an ostomy patient having an abdominal stoma, comprising:

(a) a belt assembly including an elastic belt member having an adjustable loop portion at one end thereof, and a belt connector slidably engaging the loop portion of the belt member, the belt connector releasably engaging an opposite end portion of the belt, for securing about the patient's abdomen above the stoma while maintaining tension during expansion and contraction of the patient's abdomen;

(b) a sling member formed of flexible sheet material and having front and rear wall portions, the sling member having a main side opening for receiving an ostomy pouch and a secondary side opening opposite the main side opening for permitting a portion of the ostomy pouch to extend from the sling member opposite the main side opening, the material extending between the front and rear wall portions along respective bottom extremities thereof, a horizontally disposed seam connecting the front and rear wall portions proximate upper extremities thereof, the rear wall portion of the sling member having a generally C-shaped clearance cutout extending laterally from the side opening for clearing the stoma; and (c) the sling member being connected to the belt proximate upper extremities of the front and rear wall portions, whereby the ostomy pouch is supportable proximate the patients abdomen.

\* \* \* \* \*